(12) United States Patent
Drake

(10) Patent No.: US 7,699,891 B2
(45) Date of Patent: *Apr. 20, 2010

(54) METHOD AND SYSTEM FOR TREATMENT OF REGURGITATING HEART VALVES

(76) Inventor: Daniel H. Drake, 2793 Forest Lodge Dr., Traverse City, MI (US) 49684

( * ) Notice: Subject to any disclaimer, the term of this patent is extended or adjusted under 35 U.S.C. 154(b) by 73 days.

This patent is subject to a terminal disclaimer.

(21) Appl. No.: 11/752,094

(22) Filed: May 22, 2007

(65) Prior Publication Data
US 2008/0294249 A1 Nov. 27, 2008

(51) Int. Cl.
*A61F 2/24* (2006.01)
(52) U.S. Cl. ...................... 623/2.36; 128/898
(58) Field of Classification Search ........................ None
See application file for complete search history.

(56) References Cited

U.S. PATENT DOCUMENTS

| | | | |
|---|---|---|---|
| 2002/0183839 A1* | 12/2002 | Garrison et al. | 623/2.11 |
| 2004/0131533 A1* | 7/2004 | Spacie et al. | 423/448 |
| 2004/0143323 A1* | 7/2004 | Chawla | 623/2.12 |

* cited by examiner

*Primary Examiner*—Corrine M McDermott
*Assistant Examiner*—Rebecca Straszheim
(74) *Attorney, Agent, or Firm*—John Artz; Dickinson Wright PLLC

(57) ABSTRACT

A system and process for correction of regurgitation of heart valves. With mitral valves in particular, the anterior leaflet is advanced through use of a D-plasty patch and a narrow annuloplasty ring which compresses the lateral dimension of the valve. The sizes of the patch and ring are selected to provide a sufficient advancement of the leaflet to restore the surface of coaptation.

10 Claims, 5 Drawing Sheets

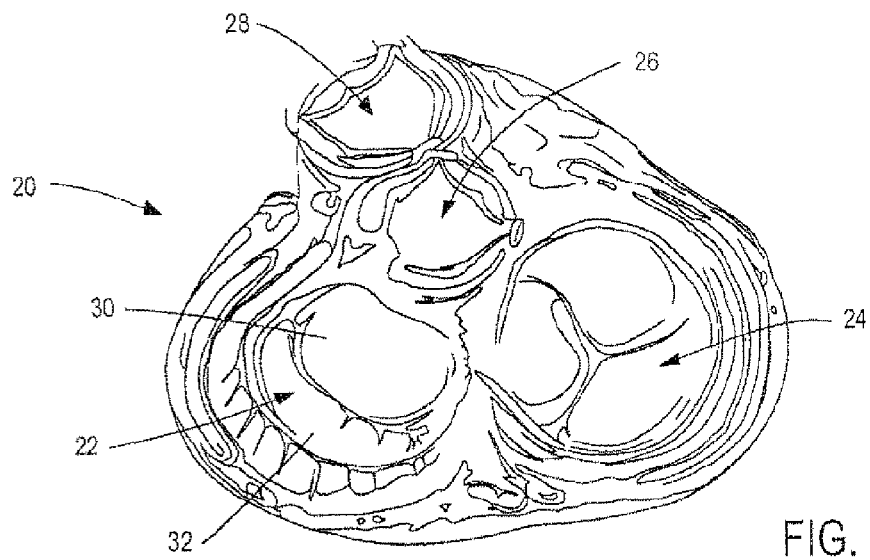
FIG. 1
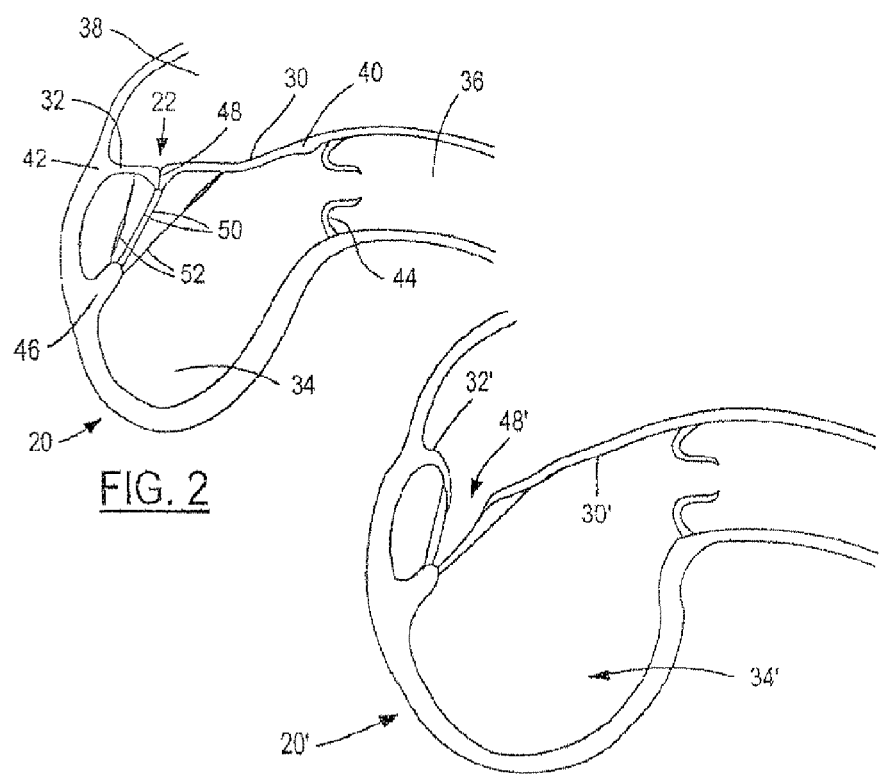
FIG. 2
FIG. 3

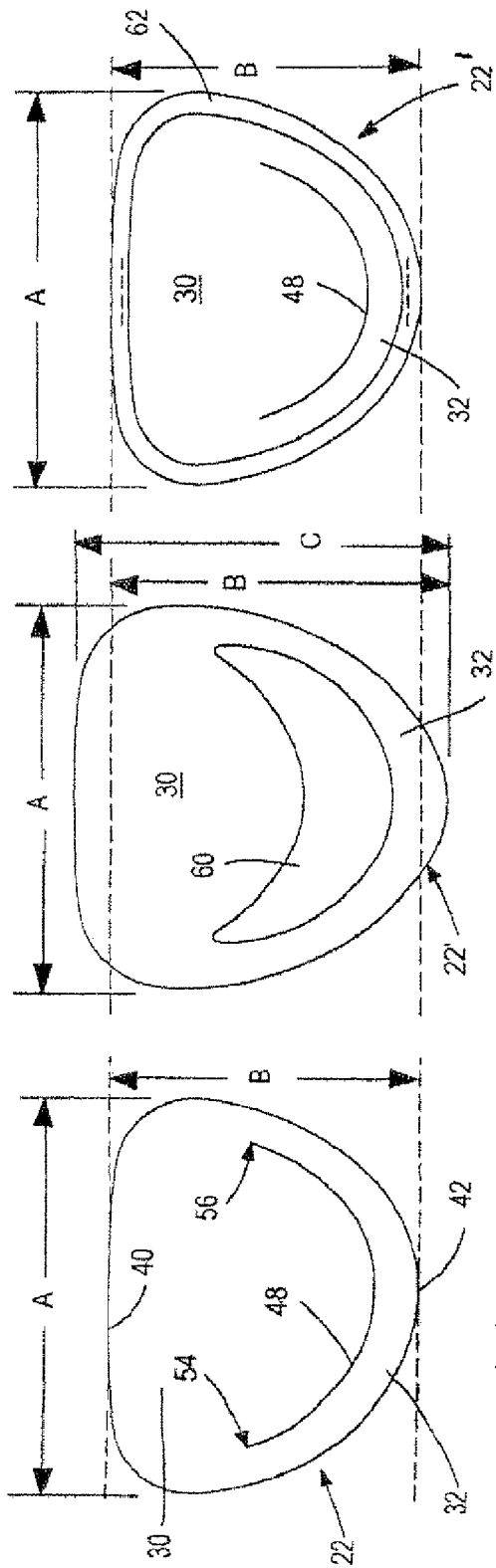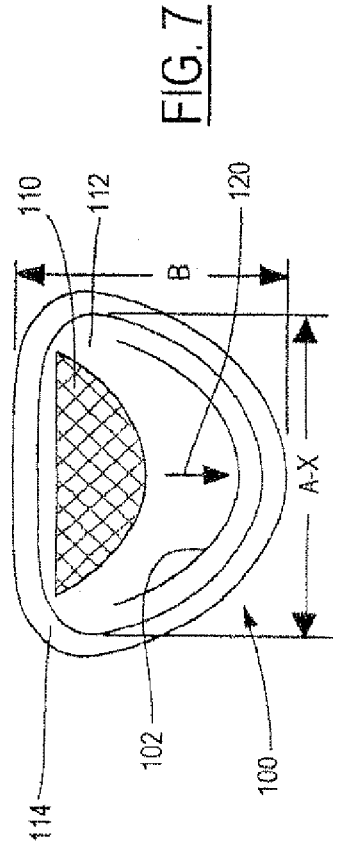

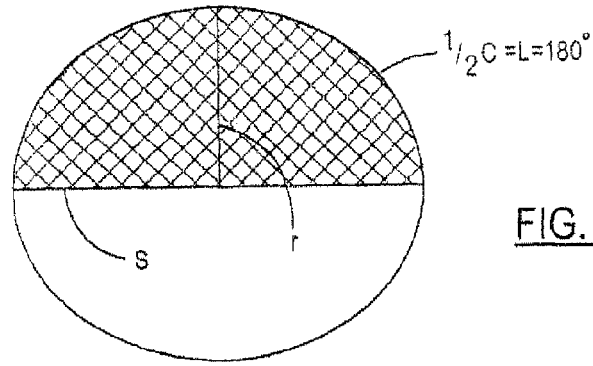
FIG. 12
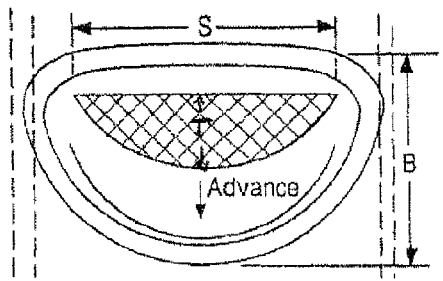
4mm reductive ring
120° D-plasty patch
S=23mm
Advance = 5.5mm
FIG. 13A
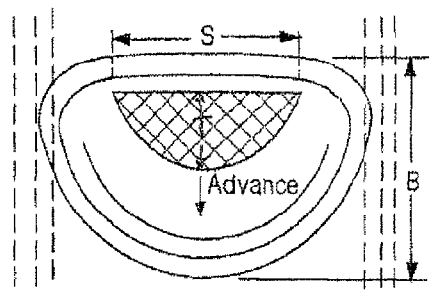
6mm reductive ring
150° D-plasty patch
S=21.5mm
Advance = 6.2mm
FIG. 13B
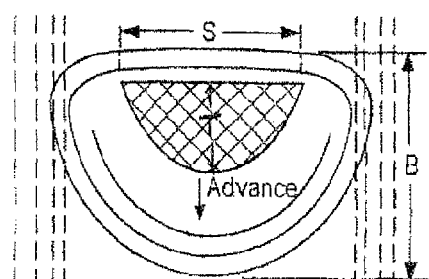
8mm reductive ring
180° D-plasty patch
S=22.0mm
Advance = 7.0mm
FIG. 13C
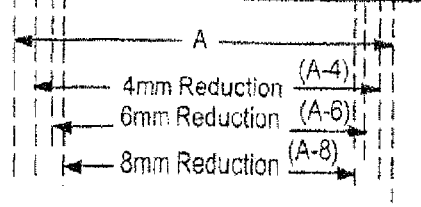

US 7,699,891 B2

METHOD AND SYSTEM FOR TREATMENT OF REGURGITATING HEART VALVES

TECHNICAL FIELD

The present invention relates to treatment of heart valves and more particularly to methods and systems for repair of regurgitating heart valves.

BACKGROUND OF THE INVENTION

A malfunction of a person's heart valve such as mitral regurgitation, can be a life threatening illness. Many systems and techniques have been developed over the years to attempt to correct the various heart valve malfunctions. These include full replacement of the valve, the use of annuloplasty rings and bands, and leaflet elongation.

Although many of these systems and techniques have been successful and have allowed patients to return to relatively normal lifestyles, there still is about a 25-30% failure rate in the repair of mitral regurgitation from a damaged and/or enlarged heart. Thus, there is a need for improved processes and systems in the area which can secure a higher rate of success.

It is thus a general object of the present invention to provide an improved process and system for the repair of heart valves. It is a more specific object of the present invention to provide an improved process and system for the repair of regurgitating heart valves, particularly hearts with mitral regurgitation (MR).

SUMMARY OF THE INVENTION

The present invention is particularly useful in the correction of regurgitating heart valves, and more particularly in the correction of mitral regurgitation (MR). The mitral heart valve is a valve which has been prone to malfunction and allow leakage of blood flow during operation of the heart. One of the reasons for MR is ventricular enlargement.

In accordance with the present invention, reductive ring annuloplasty is utilized in combination with a patch applied to the anterior leaflet. This technique compresses the heart valve tissue laterally and advances the leaflet tissue to close the valve and prevent MR.

The heart valve is first measured and analyzed and a determination is made as to the amount of lateral compression of the valve that is needed. A D-shaped plasty patch is made or selected of the appropriate size and shape for the amount of advancement needed. Once stitches are positioned around the valve for subsequent use in securing an annuloplasty ring, an incision is made on the leaflet of the mitral valve of a predetermined length.

A D-shaped plasty patch is stitched in place in the opening in the leaflet created by the incision. Thereafter, the ring is secured in place and the valve annulus is compressed to its final position. The annuloplasty ring in particular compresses the valve in the lateral direction. The advancement of the leaflet caused by such lateral compression in combination with the additional D-plasty patch extends the leaflet tissue and allows the mitral valve to close as it should during normal function.

In order to measure and provide the incision of the requisite length for the D-plasty patch, unique sizers with suture grooves and unique measuring tools are provided.

Further features, benefits and advantages of the inventive process and system will become apparent from the following description of embodiments of the invention, particularly when viewed in combination with the accompanying drawings and appended claims.

BRIEF DESCRIPTION OF THE DRAWINGS

FIG. 1 illustrates the heart in systole viewed from base with atria removed.

FIG. 2 is a schematic illustration of a cross-section of a heart depicting a normal mitral valve.

FIG. 3 is a schematic illustration of a cross-section of a heart with ventricular enlargement.

FIG. 4 schematically illustrates a normal mitral valve.

FIG. 5 schematically illustrates a mitral valve with mitral regurgitation.

FIG. 6 schematically illustrates a mitral valve with an annular ring.

FIG. 7 schematically illustrates a mitral valve repaired in accordance with the present invention.

FIGS. 10, 11 and 12 illustrate the determination and selection of D-plasty patches in accordance with the present invention.

FIGS. 13A, 13B, and 13C illustrate examples of mitral valve repairs in accordance with embodiments of the present invention.

DESCRIPTION OF PREFERRED EMBODIMENTS

Figure 8:
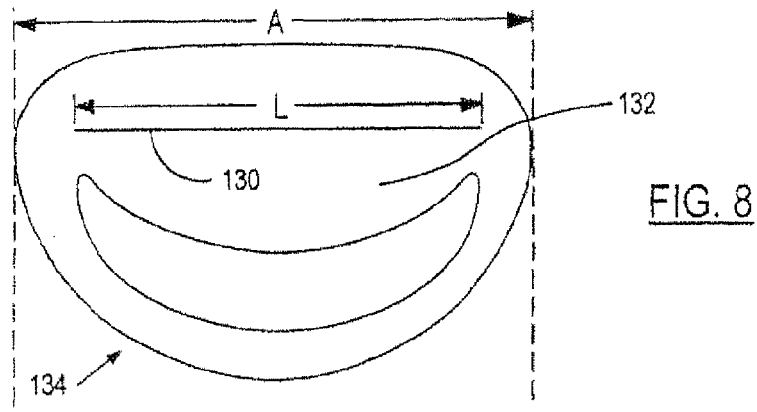
FIG. 8 schematically illustrates the initial incision step in accordance with the present invention.

The present inventive process and system has particular use and applicability for repair of mitral valves in the heart and to prevent recurrent mitral regurgitation (MR). Thus, the invention will be illustrated and described with respect to MR. It is to be understood, however, that the present invention can be used relative to repair of numerous other valves in the heart, such as tricuspid valves, aortic valves and pulmonic valves. It is also possible to use an embodiment of the present invention to secure tissue advancement in other parts of the body.

FIG. 1 is a view of a portion of a human heart 20 cut away to show the various valves. The heart 20 is viewed in systole from the base with atria removed. The valves illustrated are the mitral valve 22, the tricuspid valve 24, the aortic valve 26 and the pulmonic valve 28. The mitral valve 22 has an anterior leaflet 30 and a posterior leaflet 32.

A schematic cross-section through the left side of a normal heart 20 is shown in FIG. 2. This view is the long axis or sagittal view. The primary features of the heart as shown in FIG. 2 are the left ventricle 34, the aorta 36, and the left atrium 38, as well as the mitral valve 22. Other features include the anterior annulus 40, which connects the anterior leaflet 30 to the heart tissue, and the posterior annulus 42 which connects the posterior leaflet 32 to the heart tissue. Additional relevant features of the heart 20 shown in FIG. 2 include the aortic valve 44, the papillary muscle 46, the surface of coaptation 48, the primary chords 50 and the secondary chords 52.

One of the causes of MR is ventricular enlargement. This is shown in FIG. 3. The left ventricle 34' of the heart 20' is enlarged and creates a failure of coaptation 48'. The anterior leaflet 30' and posterior leaflet 32' are also shown in FIG. 3. The present invention provides specific processes and systems for repairing this condition, as well as other leaking (regurgitating) heart valves.

A schematic drawing of a left atrial view of a normal mitral valve 22 is shown in FIG. 4. The anterior leaflet 30 and posterior leaflet 32 meet at the surface of coaptation 48. The two ends of the surface of coaptation are the anterolateral commissure 54 and the posteromedial commissure 56. The valve 22 has a lateral annular width at the commissures labeled dimension A and a traverse anteroposterior (AP) dimension B from the anterior annulus 40 to the posterior annulus 42.

A schematic drawing of a defective mitral valve 22' with a gap 60 between the coaptive surfaces (i.e. failure of coaptation) is shown in FIG. 5. With the gap 60, the transverse dimension of the valve has been extended from B to C. This valve has MR. The anterior leaflet 30 and posterior leaflet 32 are also shown in FIG. 5.

A known way of repairing the valve 22' is to affix an annuloplasty ring 62 around the valve. This is shown in FIG. 6 which also shows the anterior leaflet 30 and posterior leaflet 32, and surface of coaptation 48. The ring 62 is secured to the annulus around the valve with a series or plurality of sutures. The ring restores the transverse dimension to its normal valve B and closes the gap. This restores the coaptive surface to its normal position.

It should be noted that typically the lateral width (lateral commissure width) A will be the same in all FIGS. 4, 5, and 6.

The method and system depicted in FIG. 6 has value in cases of mild to moderate MR. This annular ring reduction (reductive annuloplasty) is often adequate, or at least initially successful. However, regurgitation recurrence rates are high and, in more severe cases, this technique may not be adequate and may fail.

Annuloplasty rings for this purposes are available, for example, from Edwards Lifesciences LLC, and Medtronic, Inc. Edward's rings are called "Carpenter-Edwards Physio Annuloplasty Rings" and are made of layers of Elgiloy and plastic strips. The rings have a sewing ring margin that consists of a layer of silicone rubber covered by a polyester knit fabric.

The specifications for all of the commercially available annuloplasty rings from Edwards are as follows:

rior leaflet 112 and an annuloplasty ring 114 has been sutured and affixed in place around the annulus of the valve. The ring 114 has been selected having a certain lateral dimension which is less (narrower) than the lateral dimension of the annuloplasty ring typically selected and used for a valve of this particular size. In addition, the plasty patch 110 has a "D" shape which has certain dimensions selected to provide the appropriate repair. The combination of the D-plasty patch 110 and the narrower annuloplasty ring 114 advances the tissue of the anterior leaflet 112 in the direction of arrow 120. This closes the former MR gap and restores the surface of coaptation 102.

As noted in FIG. 7, the AP dimension B remains the same as the AP dimension B in FIGS. 4 and 6. However, the lateral width has been reduced from A to A-X. The amount of the reduction X is explained in more detail below.

Figure 9:
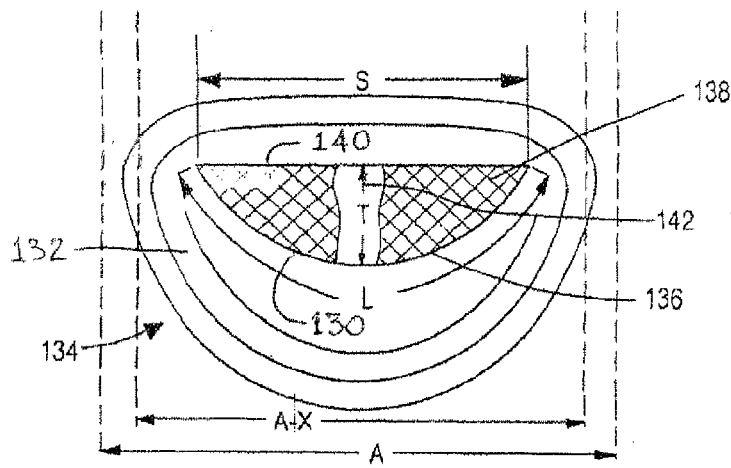
FIG. 9 schematically illustrates additional steps of a D-plasty patch and ring placement such that the mitral valve is repaired in accordance with the present invention.

In preferred embodiments of the invention, the lateral dimension A of the valve is reduced 4-8 mm and the specific D-plasty patch is selected based on the reduced dimension. This is depicted in FIGS. 8 and 9. The initial length L of the incision 130 made in the anterior leaflet 132 of the valve 134 is the same as the circumference of arc 136 of the D-plasty patch 138. This is the length of the curved surface of the "D" shaped patch. The flat or straight side of the D-plasty patch is indicated by the reference numeral 140 and has a length S. The distance 142 of the patch 138 is indicated by the letter T. This also is the amount of leaflet extension or advancement created by insertion of the D-plasty patch in the anterior leaflet.

The enhanced (i.e. narrower) prosthetic rings 160 have markings on them that correspond to the dimension S. This is shown in FIGS. 13A-C and FIG. 14. Also, it is over the distance S that compression occurs to account for the differences between the normal lateral width A of the valve and the reduced lateral width A-X, where, in the preferred embodiments, X is 4, 6 or 8 mm depending on the embodiment selected.

In this regard, for the preferred embodiments and examples provided herein, the X dimension has been selected to be 4 mm, 6 mm and 8 mm. However, it is to be understood that these amounts are merely exemplary and the invention can be utilized where X can be any reasonable dimension, such as the range from 1 mm to 10 mm.

The radius of the arc of the curved side of the D-plasty patch is "r". The length L of the incision in the anterior leaflet

| SPECIFICATIONS | | | | | | | | | |
|---|---|---|---|---|---|---|---|---|---|
| | RING SIZE (MM) | | | | | | | | |
| | 24 | 26 | 28 | 30 | 32 | 34 | 36 | 38 | 40 |
| Inner ring diameter (mm) | 22.9 | 24.9 | 26.9 | 28.9 | 30.9 | 32.9 | 34.8 | 36.8 | 38.7 |
| Outer ring diameter (mm) | 28.7 | 30.7 | 32.9 | 34.9 | 37.1 | 39.1 | 41.2 | 43.2 | 45.3 |
| Inner Elgiloy Band diameter (mm) | 24 | 26 | 28 | 30 | 32 | 34 | 36 | 38 | 40 |
| Orifice Area (mm$^2$) | 274 | 325 | 380 | 440 | 504 | 572 | 645 | 722 | 804 |

As indicated, the rings come in a range of sizes. The size is selected based on the patient's individual valve anatomy. For restrictive diseases, 24-30 mm is common.

A valve which has been repaired with the present inventive process and system is shown in FIG. 7. The valve 100 has a restored surface of coaptation 102 and MR has been eliminated. A D-plasty patch 110 has been positioned in the antecan be: $\frac{2}{3}\pi r$. This is for a reduction with one of the D-plasty patches (the 4 mm embodiment).

Figure 10:
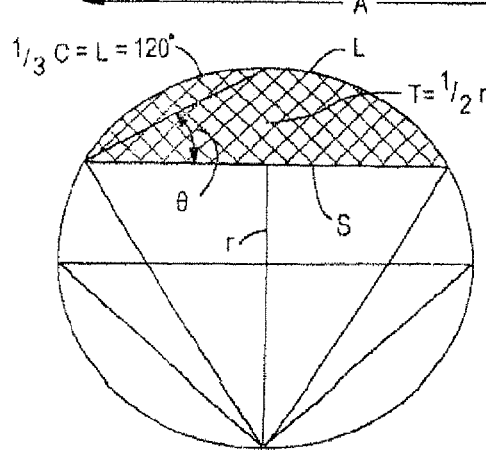
Figure 11:
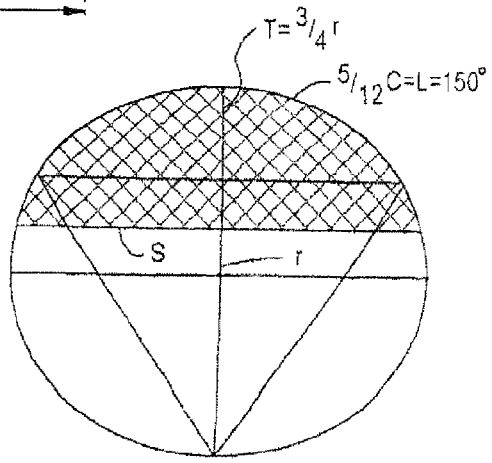

FIGS. 10-12 show how the size and dimensions of the D-plasty patch are selected for three preferred embodiments (4, 6 and 8 mm) of the invention. These Figures and accompanying empirical calculations show the length L of the incision, the distance S, the amount of advancement of the leaflet and the compression of the tissue in the area between the patch and the anterior annulus.

From an analysis of FIG. 10, where a 4 mm reduction in the size of the ring and annulus are selected, the following results are achieved:

The length L is ⅓ circumference of a circle (120°). Thus L=⅓ circumference (C)=⅔πr.
The tan θ=0.5r/0.5S=r/S=0.58. Thus S=r/0.58.
⅔πr=S+4 mm r/0.58+4 mm. Thus r=11 mm.
If r=11 mm, then L=23 mm, S=19 mm, the leaflet advance=5.5 mm, and the compression=17%

From an analysis of FIG. 11 where a 6 mm reduction in the size of the ring and annulus are selected, the following results are achieved:

The length L is 5/12 the circumference of a circle (150°). Thus L=5/12 circumference (C)=5/12 (2πr)=r/0.53+6 mm=8.2 mm.
S=r/0.53=15.5 mm
Thus, the incision L is 21.5 mm, S is 15.5 mm, the leaflet advance is 6.2 mm and the compression=28%.

From an analysis of FIG. 12 where an 8 mm reduction in size of the ring and annulus are selected, the following results are achieved:

The length L is ½ the circumference (C) of a circle (180°) πr=2r+8 mm and r=7 mm
S=2r=14 mm
Thus, the incision L is 22 mm, S is 14 mm, the leaflet advance is 7 mm and the compression=36%.

FIGS. 13A, 13B and 13C schematically illustrate the three embodiments discussed above. In these three FIGS. A-4 refers to the 4 mm reduction dimension, A-6 refers to the 6 mm reduction dimension, A-8 refers to the 8 mm redaction dimensions and B refers to the traverse anteroposterior dimension.

Since 1 mm of additional material is proved around the outside of the patch to allow for patch and tissue compression with suturing, the actual patch will measure 2 mm larger in the S and T dimensions. Thus, the resultant D-plasty patches for the three examples are:

FIG. 10: S=21 mm and L=25 mm;
FIG. 11: S=17.5 mm and L=23.5 mm; and
FIG. 12: S=16 mm and L=24 mm.

Figure 14:
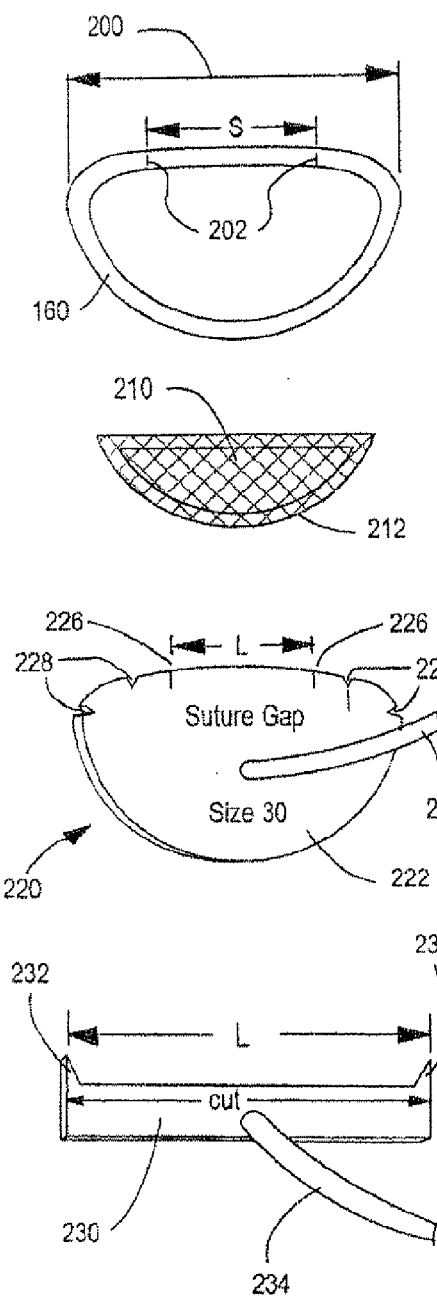
FIG. 14 illustrates devices and tools for use with the embodiments of the present inventive process and system.

In order to assist the surgeon in performing the unique process and using the unique system in accordance with the present invention, a series or kit of rings, D-plasty patches and tools are preferably provided. These are shown in FIG. 14.

As indicated above, a series of annuloplasty rings 160 are provided which are narrower in width 200 than the size of the annulus. The rings can be in increments of 1 mm to 10 mm narrower, with several rings having the preferred sizes of 4 mm, 6 mm and 8 mm narrower. In addition, each of the rings 160 has markings 202 thereon which correspond to the distance S of the corresponding D-plasty patch.

A series or set of D-plasty patches 210 are also provided in the kit. At least one D-plasty patch of the requisite size and shape (as determined mathematically in the manner set forth above) should be provided for each size of annuloplasty rings in the kit. The set should have several patches corresponding to the dimensions set forth above in the three embodiment examples. Preferably the patches also have a sewing margin 212 marked on each of them. The patches can be either biological or synthetic, that is, they can be made from natural tissue material of the patient or other animal or plant derivation, or can be made from a synthetic material such as Dacron or Gortex.

A set or series of sizer tools 220 are also provided. The sizers tools each have a flat plate 222 and a handle member 224. The sizer tools have appropriate markings 226 to facilitate ring and patch placement, as well as suture grooves 228 for sizing. The sizer tool 220 shown in FIG. 14 is marked with the appropriate size ("size 30"). The entire set of sizers could include a series of 20-30 sizer tools, each having a slightly different size and/or L markings.

In addition, a set or series of measuring tools 230 are provided. The measuring tools each have a pair of pointed projections 232, or equivalent markings, which are spaced apart the distance L. A handle 234 facilitates the use of the tool.

Figure 15:
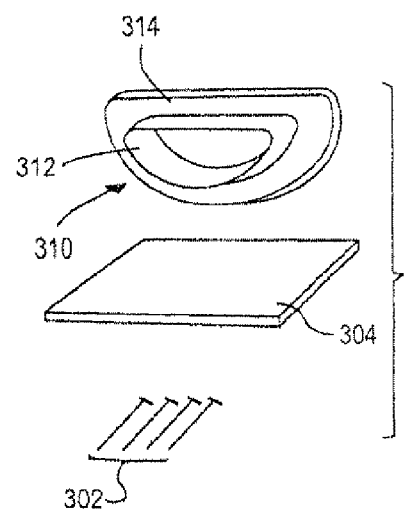
FIGS. 15 and 16 depict a procedure for preparing D-plasty patches from tissue.
Figure 16:
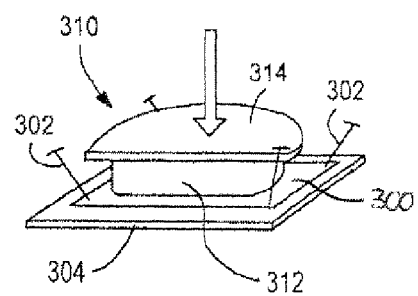

As indicated above, one of the preferred materials for the D-plasty patches is the patient's own tissue. Preferably, this material is the pericardium which is harvested from the patient shortly after the chest is opened for the valve repair operation. Once the tissue 300 is harvested, it is flattened, gently stretched and held in place by pins or tacks 302. This is shown in FIGS. 15 and 16. The tissue can be tacked to a small plank (or "anvil") 304. The tissue is then preserved, such as by a gluteraldehyde fixation process. Once the process is complete and the pericardium is rinsed and cleaned, it is cut into the proper size and shape, preferably by a cutting instrument such as the pericardial D-patch cutter 310. The cutter 310 has a D-shape, the particular "D-shape" being selected in accordance with the mathematical formula and procedure discussed above. The cutter includes a sharpened steel cutting edge 312 in the shape of the patch and a mounting plate 314 for hand protection. Preferably, a series of cutters are provided in the kit, such as ten cutters representing valve repair in accordance with the present invention utilizing annuloplasty rings 1-10 mm narrower than conventional rings.

The present invention provides a significantly valuable and beneficial process and system for repairing or correcting heart valves (particularly the mitral valve) which have a gap or do not close completely and which allow regurgitation of the blood flow. In order to perform the inventive process, the patient is connected to a heart-lung machine and placed on cardiopulmonary bypass. The heart is prepared for the operation with an aortic cross-clamp and cardioplegic arrest.

Prior to the surgery, the patient is given a full evaluation by the surgeon and the amount of lateral compression and anterior leaflet advancement are determined. Typically, echocardiography is utilized for this purpose. Thus, the annuloplasty ring and D-plasty patch are selected and determined before the surgery has begun. The ring and patch size are selected to restore the surface of coaptation for the particular patient.

Once the atrium is opened and the mitral valve exposed, possible secondary chord lysis is performed as may be necessary. Then, using the measuring tool 230, the distance L is determined on the anterior annulus. Annular stitches are placed around the valve in preparation for the selected annuloplasty ring except in the area of the annulus indicated by the distance L.

An incision is then made having length L for the D-plasty patch. The measuring tool 230 is used for this purpose. Any desired additional secondary chord lysis can be performed at this point.

The remaining annular sutures are then placed in the space L initially left in the ring outline. Then the D-plasty patch is sewn in place. Preferably, the patch is first anchored with stitches at each lateral end; then the upper and lower edges of the patch are secured in place with running stitches. If desired, temporary stitches can be positioned at various points on the edges of the patch to hold it in place when the running stitches are sewn in place. After the patch is sewn tightly in place, the temporary stitches are removed.

After the patch is secured in place, the annuloplasty ring is then secured in place. The sutures previously positioned around the annulus are drawn through the fabric or edges of the ring and the ring is tightly secured in place around the valve. This restores and compresses the valve in all directions to its final position. The leaflet returns to its normal orientation with the D-plasty patch in it. The surface coaptation is restored and the coaptive surfaces of the commissures are unchanged.

Once the valve is repaired, the heart is deaired and the atrium is closed. The patient is taken off the heart-lung machine and the patient's heart is returned to its normal operation.

While preferred embodiments of the present invention have been shown and described herein, numerous variations and alternative embodiments will occur to those skilled in the art. Accordingly, it is intended that the invention is not limited to the preferred embodiments described herein but instead limited to the terms of the appended claims.

What is claimed is:

1. A method for treatment of regurgitating heart valves, said method comprising the steps of:
   evaluating a patient and determining the repair necessary to prevent regurgitation;
   selecting a plasty patch and annuloplasty ring requisite for the repair;
   making an incision in the heart valve leaflet for placement of the plasty patch;
   securing the plasty patch in said incision to advance the leaflet toward coaptation;
   prior to securing said plasty patch in place positioning a plurality of sutures around said heart valve for future securing of an annuloplasty ring; and
   securing an annuloplasty ring around the heart valve to laterally compress the head valve and to support the leaflet advancement toward coaptation;
   said annuloplasty ring being narrower in the lateral commissure dimension than an annuloplasty ring which would have formerly been selected to repair regurgitation.

2. The method for treatment of regurgitating heart valves as described in claim 1 wherein said plasty patch is a D-shaped plasty patch having a straight side and a curved arcuate side.

3. The method for treatment of regurgitating heart valves as described in claim 2 wherein said incision in the head valve leaflet is the same length as the length of the curved arcuate side of said D-shaped plasty patch.

4. The method for treatment of regurgitating heart valves as described in claim 2 wherein a gap is left in said plurality of sutures corresponding to the length of said curved arcuate side of said 0-shaped plasty patch.

5. The method for treatment of regurgitating head valves as described in claim 1 wherein said narrower dimension of said selected annuloplasty ring is in the range of 1 mm 10 mm.

6. The method for treatment of regurgitating heart valves as described in claim 5 wherein said narrower dimension of said selected annuloplasty ring is in the group of 4 mm, 6mm and 8 mm.

7. The method for treatment of regurgitating heart valves as described in claim 1 wherein a gap is left in said plurality of sutures, said gap having a dimension corresponding to the length of said incision.

8. The method for treatment of regurgitating heart valves as described in claim 1 wherein said annuloplasty ring has markings thereon corresponding to the length of said incision, said marking being used to indicate where sutures are not to be initially positioned around the head valve for future placement of said annuloplasty ring.

9. A method for treatment of regurgitating heart valves, said method comprising the steps of:
   evaluating a patient and determining the repair necessary to prevent regurgitation;
   selecting a plasty patch and annuloplasty ring requisite for the repair;
   making an incision in the head valve leaflet for placement of the plasty patch;
   positioning a plurality of sutures around the head valve for future securing of an annuloplasty ring, said plurality of sutures having a gap having a dimension corresponding to the length of said incision;
   securing the plasty patch in said incision to advance the leaflet toward coaptation; and
   securing an annuloplasty ring around the head valve to laterally compress the head valve and to support the leaflet advancement toward coaptation.

10. A method for treatment of regurgitating heart valves, said method comprising the steps of:
    evaluating a patient and determining the repair necessary to prevent regurgitation;
    selecting a plasty patch and annuloplasty ring requisite for the repair;
    making an incision in the heart valve leaflet for placement of the plasty patch;
    securing the plasty patch in said incision to advance the leaflet toward coaptation; and
    securing an annuloplasty ring around the heart valve to laterally compress the heart valve and to support the leaflet advancement toward coaptation;
    wherein said annuloplasty ring has markings thereon corresponding to the length of said incision, said markings being used to indicate where sutures are not to be positioned around the heart valve for placement of said annuloplasty ring.

* * * * *

UNITED STATES PATENT AND TRADEMARK OFFICE
CERTIFICATE OF CORRECTION

PATENT NO. : 7,699,891 B2  Page 1 of 1
APPLICATION NO. : 11/752094
DATED : April 20, 2010
INVENTOR(S) : Daniel H. Drake It is certified that error appears in the above-identified patent and that said Letters Patent is hereby corrected as shown below:

Column 8, Line 3: "1 mm 10 mm" should read -- 1 mm - 10 mm --.

Signed and Sealed this
Fourteenth Day of February, 2012

David J. Kappos
*Director of the United States Patent and Trademark Office*